Dec. 13, 1960 O. O. DUNHAM Plant Pat. 2,002
CHRYSANTHEMUM PLANT
Filed July 27, 1959
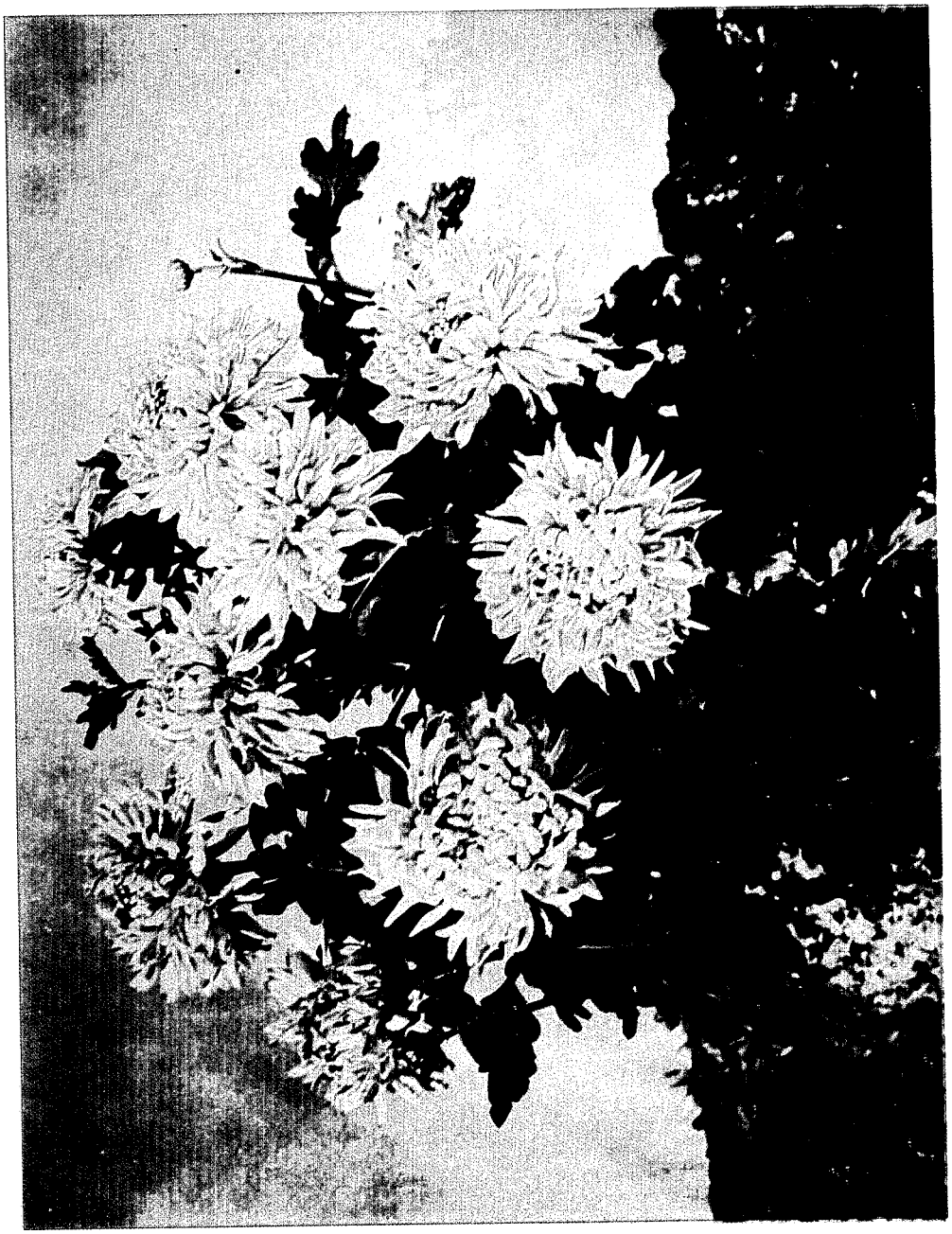
Inventor
O. O. Dunham
by Robbs & Robbs
attorneys United States Patent Office Plant Pat. 2,002
Patented Dec. 13, 1960

2,002

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,944

1 Claim. (Cl. 47—60)

My present invention comprises a new and distinct variety of chrysanthemum plant, which is the result of crossing the variety of my own introduction, which I designate "Truly Yours," an unpatented variety, and another unpatented variety of my own introduction known as "Peaceful."

The object of my invention has been to produce a new variety of chrysanthemum plant which will have very large blossoms and a color somewhat resembling the parent variety "Truly Yours," the color being a combination of moderate pink and strong orange color (Nickerson Color Fan produced by Munsell Color Company).

The development of the present variety is the result of a program which I have conducted involving careful selection and cross-breeding to produce new varieties of chrysanthemums, which new varieties will include the important and desirble characteristics of both parents which are broadly speaking American garden chrysanthemums and English early chrysanthemums, with different desired colors derived from the parents.

An actual result of the hybridization above generally referred to, is production of this present new and distinct variety of chrysanthemum plant, characterized by the moderate pink to strong orange color of its blooms, the fully double arrangement of its petals, the very large size of blooms, the tall upright, habit of growth and the early, continuous and long blooming period.

More specifically, the general impression created by my plant when viewed from a distance is of a moderate pink color when the blooms are fully blown, with the plant having a tall upright habit.

While my new variety derives its color from the pollen parent "Truly Yours" the tall upright plant habit is derived from the seed parent "Peachful." The upright habit is better than the habit of either the pollen or seed parent, and the flower type is an improvement over both of the parents.

Under conditions of culture in the region of Niles, Michigan, plants of my new variety produce very large blooms, averaging when fully expanded some seven inches in diameter. The blooms are borne in clusters and somewhat irregularly but the stems are long and strong. The bloom retains its general form to the end and the petallage is very double with innumerable petals thereon.

When the plants are grown in the region of Niles, Michigan, they bloom very early, usually in mid-September, and have a continuous flowering feature of English early chrysanthemums, in contrast to the American garden chrysanthemums which bloom all at one time over a short period and then do not bloom subsequently. While the English early chrysanthemums are somewhat irregular in flowering the instant seedling is better adapted to continuous flowering habits.

One of the aspects of the color of the blooms is the fact that after a light frost, the color appears to be intensified.

The flowers of the new variety are of a strong purplish red when the petals begin to unfurl and when half blown the inside of the petals appear to be washed with deep purplish pink and the reverse of the petals with a light purplish pink. When the flower is fully blown the center of the flower appears to be a strong orange and the general tonality from a distance is of the moderate pink.

My new variety has been asexually reproduced by cuttings, in the vicinity of Niles, Michigan.

My new variety has been found to retain its distinctive characteristics through successive asexual reproductions.

The accompanying drawing, forming a part hereof, shows a typical plant of my new variety of chrysanthemum.

The following is a detailed description of my new variety of chrysanthemum plant, the color references being to the Nickerson Color Fan produced by Munsell Color Company:

Parentage: Seedling.
*Seed parent.*—"Peaceful" (unpatented).
*Pollen parent.*—"Truly Yours" (unpatented).
Classification: Botanic—*Chrysanthemum indicum.*

*Flower*

Blooming habit: Blooms profusely, early, as from mid-September until killing frost, producing a continuous display of blooms during such period, the observations of the colors being made at Niles, Michigan, in October.

Bud:
*Size.*—Large.
*Form.*—Short with flat top. Not affected by hot or wet weather. Sepals of no consequence.
*Color.*—When petals begin to unfurl—7.5RP 5/12 strong purplish red. When half blown: inside of petals—washed with 7.5RP 6/12 deep purplish pink; reverse of petals—7.5RP 8/5 light purplish pink.
*Peduncle.*—Very long.
*Aspect.*—Rough.
*Color.*—Medium green.
*Strength.*—Stiff; erect.
*Opening.*—Bud opens well; somewhat affected by adverse conditions.

Bloom:
*Size.*—Very large.
*Average size when fully expanded.*—7 inches (disbudded).
*Borne.*—In clusters—irregular.
*Stems.*—Long; strong.
*Form.*—When first opened—flat. Permanence—retains its form to the end.
*Petalage.*—Very double. Number of petals under normal conditions—innumerable.
*Color.*—Center of flower—2.5YR 7/10 Munsell Hue 2.5YR. Outer petals—2.5R 9/3 Munsell Hue 2.5R. Base of petals (singlet)—2.5R 6/11 Munsell Hue 2.5R. Inside of petals—2.5R 6/11 Munsell Hue 2.5R. Reverse of petals—2.5R 9/3 Munsell Hue 2.5R. General tonality from a distance—2.5R 8/5 Munsell Hue 2.5R.
*Discoloration.*—First week—retains much the same color. Second week—retains somewhat the same color. Third week—retains somewhat the same color. Light frost tends to intensify color.

Petals:
*Texture.*—Thin. Affected by hot weather by bleaching. In wet weather it may have a tendency to get fungus infection.
*Appearance.*—Velvety inside—satiny outside.
*Form.*—Pointed.
*Arrangement.*—Imbricated.
*Lastingness.*—On the plant—very long. As cut flower—long.

Genital organs:

*Stamens, anthers.*—Small; few. Color—yellow. Arrangement—regular around styles.

*Stamens, filaments.*—Short. Color—white.

*Styles.*—Columnar. Length—short.

*Stigmas.*—White.

*Ovaries.*—All enclosed in calyx.

Fruit: Variety is fertile with its own pollen.

*Form.*—Oblong shaped.

*Aspect.*—Rough.

*Color at maturity.*—Brownish grey.

*Plant*

Form: Bush.

Growth: Vigorous; upright, branching, compact.

Foliage:

*Size.*—Large.

*Quantity.*—Abundant.

*Color.*—New foliage: upper side—normal green; under side—light green. Old foliage: upper side—dark green; under side—dark green.

*Shape.*—Three lobed.

*Texture.*—Upper side—smooth; flat. Under side—smooth. Ribs and veins—ordinary.

*Edge.*—Smooth.

*Leaf stem.*—Green in color. Under side—smooth.

*Stipules.*—Short.

*Disease resistance.*—Under certain conditions susceptible to mildew.

I claim:

A new and distinct variety of chrysanthemum plant substantially as herein disclosed, characterized as to novelty by the moderate pink and strong orange color of its blooms, the fully double arrangement of its pedals, the very large size of its blooms, the tall upright habit of growth, and the early, continuous and long blooming period.

No references cited.